(12) United States Patent
Gilbert

(10) Patent No.: US 7,338,646 B2
(45) Date of Patent: Mar. 4, 2008

(54) METHOD AND APPARATUS FOR DISINFECTING ITEMS

(75) Inventor: David Gilbert, London (GB)

(73) Assignee: Roteck Limited, London (GB)

( * ) Notice: Subject to any disclaimer, the term of this patent is extended or adjusted under 35 U.S.C. 154(b) by 611 days.

(21) Appl. No.: 10/485,411

(22) PCT Filed: Aug. 1, 2002

(86) PCT No.: PCT/GB02/03537

§ 371 (c)(1),
(2), (4) Date: Jan. 30, 2004

(87) PCT Pub. No.: WO03/012228

PCT Pub. Date: Feb. 13, 2003

(65) Prior Publication Data

US 2004/0223894 A1     Nov. 11, 2004

(30) Foreign Application Priority Data

Aug. 1, 2001 (GB) ............................... 0118774.9

(51) Int. Cl.
*A61L 2/00* (2006.01)
*A45C 13/22* (2006.01)
(52) U.S. Cl. ..................... 422/292; 16/412; 16/417
(58) Field of Classification Search ............... 422/292; 16/412, 417
See application file for complete search history.

(56) References Cited

U.S. PATENT DOCUMENTS 3,314,746 A * 4/1967 Millar .................. 422/186
3,749,290 A * 7/1973 Micallef ................ 222/207
4,171,776 A * 10/1979 Pagliaro ................ 239/274
5,152,461 A * 10/1992 Proctor ................. 239/304
5,314,668 A   5/1994 Biermaier
6,211,788 B1  4/2001 Lynn et al.
6,364,172 B1* 4/2002 Maas et al. ............ 222/383.1

FOREIGN PATENT DOCUMENTS

| CH | 568 074     | 10/1975 |
|----|-------------|---------|
| DE | 198 57 268  | 6/2000  |
| DE | 200 01 422  | 6/2000  |
| EP | 0 351 307   | 1/1990  |
| EP | 1 412 597   | 8/1992  |
| NL | 8701311     | 1/1989  |
| WO | WO-03/012228| 2/2003  |

* cited by examiner

Primary Examiner—Gladys J P Corcoran
Assistant Examiner—Kevin Joyner
(74) Attorney, Agent, or Firm—Jon A. Gibbons; Fleit Kain Gibbons Gutman Bongini & Bianco P.L.

(57) ABSTRACT

Method and apparatus for disinfecting an item, for example, a handle for a door or a tap in a toilet facility. The apparatus includes a movable member, e.g., a door handle having a contact surface for being manually engaged to move the movable member; germicide applying means for applying germicide to the surface; and an operating mechanism coupled between the movable member and the germicide applying means and operable in response to movement of the movable member for applying germicide to the contact surface after movement of said movable member. The germicide applying means may be a pump. The operating mechanism may act to prime the pump when the door handle is turned to open the door. The germicide is sprayed over the handle after the handle is released and returns to its initial position. The return movement may be retarded.

9 Claims, 8 Drawing Sheets

METHOD AND APPARATUS FOR DISINFECTING ITEMS

CROSS-REFERENCE TO RELATED APPLICATIONS

This application is based upon and claims priority from PCT/GBO2/03537, filed on Aug. 1, 2002, which is based on and claims priority from British Application 0118774.9 filed on Aug. 1, 2001, the entire disclosure of each of the aforementioned applications are each herein incorporated by reference in their entirety.

FIELD OF THE INVENTION

This invention relates to a method and apparatus for disinfecting items. More particularly, but not exclusively, the invention concerns a handle, for example, a door handle, tap handle, or toilet cistern handle which has means to apply thereto a sterilising substance, such as a bactericide/disinfectant, subsequent to use of the article to which the handle is attached.

BACKGROUND OF THE INVENTION

It is well known that bacteria and other germs can be transferred between surfaces by human contact. Further, it is also known that human contact with a bacteria- or germ-laden surface can cause potentially infectious agents to be transferred to the human. Dirty or unclean surfaces can also become active breeding grounds for bacteria and other germs.

Whilst most people appreciate the benefits of washing their hands subsequent to using toilet facilities, some do not. In such cases, there is obviously a risk that a potentially infectious agent will be transferred from the unwashed hand to a surface. Such a surface may be a door handle used to open the door to the toilet facilities. Further, even if a person does wash their hands, a previous user may not have, thereby providing an opportunity for an agent to be transferred from a germ-laden door handle to the hand of the person who did wash their hands. These problems may be particularly acute in schools or in hospitals, although all toilet facilities suffer in this fashion.

Even when one washes one's hands, the tap or faucet is usually hand operated. This necessitates one's germ-laden hands contacting the tap, thereby potentially transferring those germs. After washing one's hands to clean them of any agents, one then has to turn the tap off, providing an opportunity for re-infection of one's hands. In hospital surgery units, this problem is alleviated by having either electronically activated taps, or by turning the tap on and off using one's elbow, actuating a specially adapted tap extension.

CH 568074 discloses a hollow handle in which is located a spongy material impregnated with disinfectant. Also housed within the cavity is a weight. As the handle is turned, the weight compresses the spongy material, forcing a small amount of disinfectant out of an aperture in the handle and onto the hand of the handle operator.

EP-A1-0351307, discloses a device in which the action of using a handle causes it to be axially reciprocated subsequent its release by the operator. During the reciprocating motion, an aseptisising product is applied thereto. DE-U-20000432 and DE-U-20001422 similarly provide handles which have disinfectant applied thereto, subsequent to their operation.

Accordingly, a need exists to overcome the problems and shortcomings of the prior art to provide a handle which can be used in a variety of situations, and in both high and low traffic zones and which effectively cleanses the handle. It is a further object to provide a self-sterilising handle of simple construction which has no need for electricity or other external power sources. It is a further object of the invention to provide a sterilising device which effectively exposes the gripping or actuation surfaces of a handle to a germicidal agent. It is another object that the hand of the handle operator is not exposed to the disinfecting agent.

SUMMARY OF THE INVENTION

According to one aspect of the present invention, there is provided an apparatus comprising a movable member, a contact surface engageable manually to move the movable member from a first to a second position, the member returning to its first position upon release of the contact surface, germicide applying means for applying germicide to the contact surface; and an operating mechanism coupled between the movable member and the germicide applying means to cause germicide to be applied to the contact surface, characterised in that the operating mechanism is operable during the return movement of the movable member to the first position to deliver a spray of an aerosol or mist of germicide onto the contact surface.

In the preferred embodiment of the invention, means are provided for retarding the return of the movable member to the first position after manual release of the contact surface. In this way, it is ensured that the handle has been manually released before it is sprayed.

The germicide applying means may conveniently comprise a reservoir for containing the germicide and a pump connected between the reservoir and an outlet for spraying onto the surface germicide received from the reservoir means via the pump.

Advantageously, the operating mechanism is operable to prime the pump with germicide during the movement of the movable member from the first to the second position.

In preferred embodiment of the invention, the pump has an operating element movable to prime the pump and further movable to eject germicide, the operating mechanism being operable in response to the movement and the return of the movable member to move the operating element of the pump.

The operating mechanism may suitably comprises a camming member mounted for turning movement in response to the movement and the return of the movable member, the camming member having a camming surface engaged with the operating element.

In accordance with a second aspect, the invention provides a self-sterilising handle assembly for a door or the like comprising a manually operable handle and a spray head, the handle being operable to open the door or the like, characterised in that the handle is arranged upon its manual release subsequent to operation of the door or the like, to cause the spray head to spray germicide over at least part of the handle.

In this specification, the terms "germicide" and "germicidal agent" are used to indicate an agent which is noxious to bacteria, viruses and other germs and/or which disinfects or tends to sterilise the surfaces with which it comes into contact.

The germicidal agent may comprise isopropyl alcohol (IPA), a germicidal concentration of chlorine containing substances, e.g. an aqueous solution of sodium hypochlorite or chlorhexidines, a solution of tea tree oil or other known germicidal substances such as iodophores, solutions of quaternary ammonium salts, phenols and aldehydes. It may also be selected to evaporate subsequent to its application to the handle means.

The source of germicidal agent is preferably a reservoir, housing the germicidal agent, in fluid connection with the delivery means. The reservoir may be removably mounted to the assembly, preferably being releasably secured thereto by means of a lock. The walls of the reservoir may be translucent or clear so that the level or amount of germicidal agent remaining therein is determinable by visual inspection and the act of drawing the liquid and spraying it is conspicuous to the user.

The assembly may further comprise a light and/or a phosphorescent panel to render at least part of the assembly visible in the absence of an external light source. The reservoir may be composed of a phosphorescent material.

BRIEF DESCRIPTION OF THE DRAWINGS

The subject matter, which is regarded as the invention, is particularly pointed out and distinctly claimed in the claims at the conclusion of the specification. In order that the invention may be better understood, embodiments thereof will now be described by way of example only and other features, and advantages of the invention will be apparent from the following detailed description taken in conjunction with reference to the accompanying drawings, in which:

DESCRIPTION OF THE PREFERRED EMBODIMENTS

It should be understood that these embodiments are only examples of the many advantageous uses of the innovative teachings herein. In general, statements made in the specification of the present application do not necessarily limit any of the various claimed inventions. Moreover, some statements may apply to some inventive features but not to others. In general, unless otherwise indicated, singular elements may be in the plural and vice versa with no loss of generality.

Figure 1:
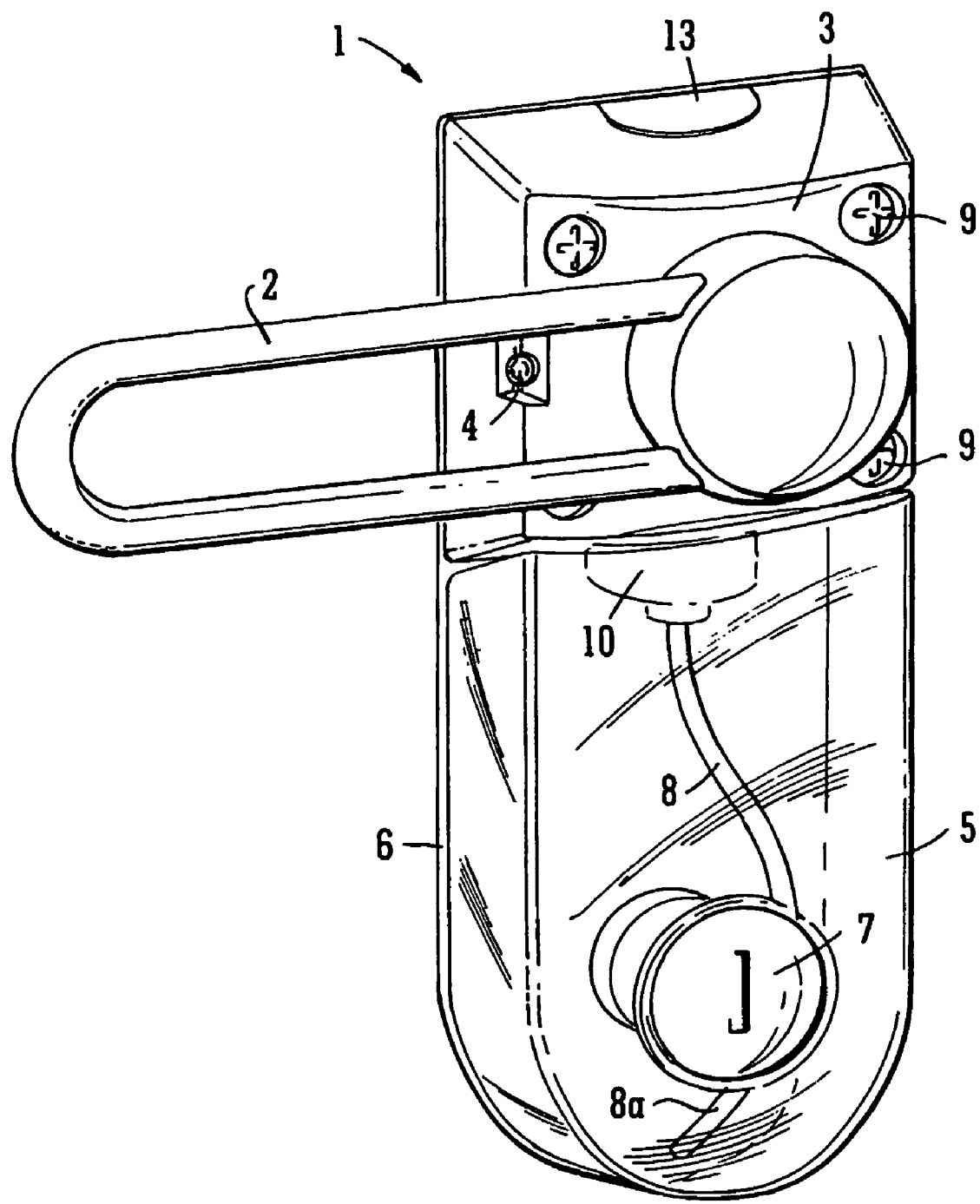
FIG. 1 is a perspective view of a first embodiment of handle assembly.

Referring firstly to FIG. 1, there is shown a handle assembly 1 for a door having a pivotable handle 2, a housing 3 and a reservoir 5 for holding a germicidal agent. Projecting from the housing 3 is a spray head 4. Suitable spray heads 4 spray liquids, although aerosol heads or nebulizers, which provide an aerosol or fine mist respectively, are preferred. The housing 3 and the reservoir 5 are mounted on a plate 6. A tab 13 is provided in the housing 3.

The reservoir 5 is translucent so that the contents can be viewed and is provided with a lock 7 to secure it to the plate 6.

A tube 8 extends from the bottom of the reservoir 5 to a delivery device 10 and at the bottom of the reservoir.

Figure 2A:
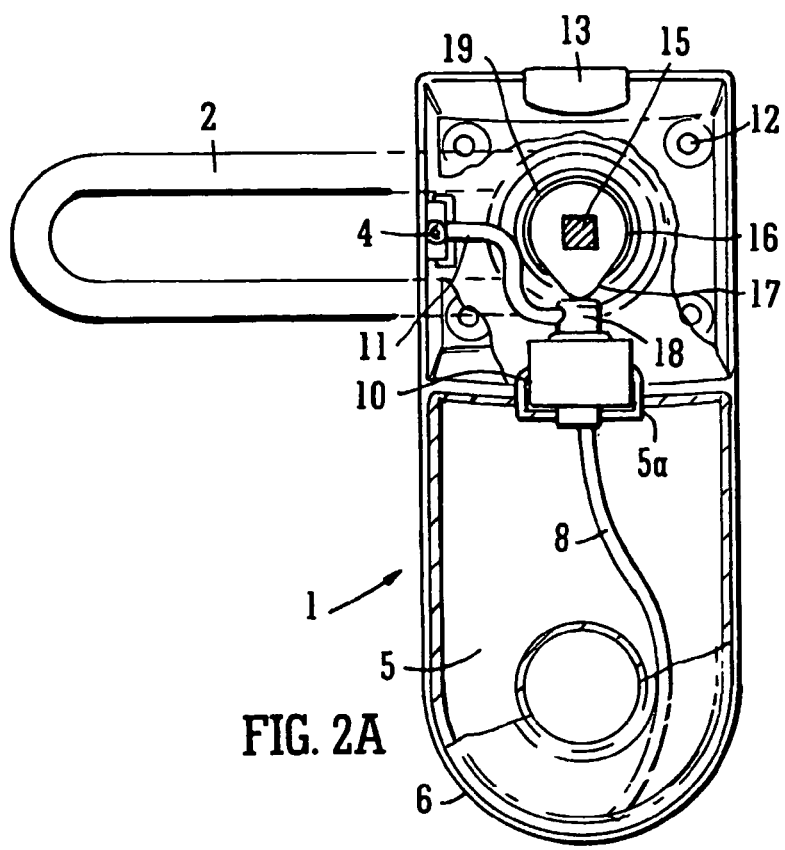
FIGS. 2A and 2B are partial cut-away elevations of the handle assembly of FIG. 1.

As seen in FIG. 2A, the delivery device 10 is in fluid connection with the spray head 4, by means of a short, flexible tube 11.

Apertures, such as screw holes 12, are provided in the housing 3 which register with holes in the plate 6. The handle assembly 1 is attached to a door by a plurality of screws 9 or the like, which extend through the holes 12 in the housing 3 and those in the plate 6. (These may be covered by a plate or housing to prevent vandals removing the device.)

The reservoir 5 is connected to the plate 6 by the provision of extension portions (not shown) which allow disconnection of the reservoir 5 from the plate 6 by a simple lift-and-pivot action. The delivery device 10 is located within a recessed portion 5a of the reservoir 5.

In FIG. 2A, the handle 2 is shown in its rest position, with the door closed, a latch (not shown) being received within an aperture (also not shown) in the doorframe (not shown), as is well known. As can be seen, the handle 2 is connected to a spindle 15, rotation of which causes the door latch to withdraw from, or extend in to, the aperture of the door frame.

Mounted about the spindle 15 is a part circular member 16, defining a cam surface 17. As shown, the cam surface 17 engages the upper surface of a pump member 18 of the delivery device 10. Also provided is a torsion spring 19 which urges the handle 2 and part circular member 16 into the condition shown in FIG. 2A.

Figure 2B:
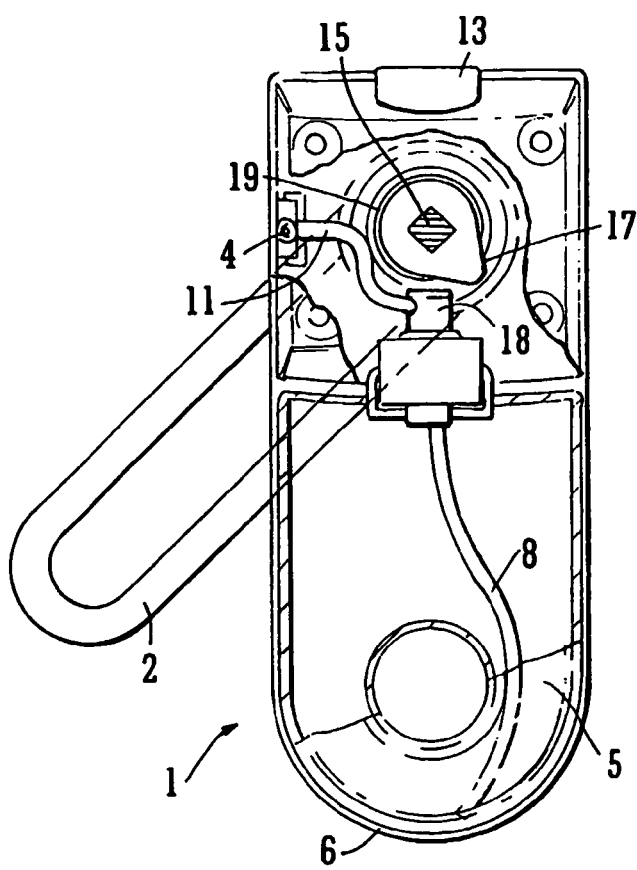

The pump head 18 is resiliently urged into the extended condition shown in FIG. 2B by an internal compression spring (not shown).

FIG. 2B shows the handle 2 in a position where it has been rotated about the spindle 15, against the urging of the torsion spring 19. Rotation of the handle 2 causes a simultaneous rotation of the part circular member 16, causing the cam surface 17 to disengage the pump head 18 and thereby allowing the pump head 18 to rise, in response to the urging of the internal compression spring (not shown).

As the pump head 18 rises to the position shown in FIG. 2B, a charge of the germicidal agent held in the reservoir 5 is drawn up tube 8, forcing some germicidal agent into tube 11. A non-return valve (not shown) is provided in the flow path, within delivery device 10, between the tubes 8 and 11.

As the handle 2 is released, the torsion spring 19 causes it to return to the position shown in FIG. 2A, thereby bringing the cam surface 17 into engagement with the upper surface of the pump head 18. The depression of pump head 18 forces the charge of germicidal agent held in the tube 11 out of the spray head 4. As the charge is forced out of the spray head 4, it becomes an aerosol, or is at least nebulized, whereupon it is sprayed over the handle 2, coating the surfaces thereof with germicidal agent.

It will be appreciated that to open a door fitted with this assembly 1, the user will grasp the handle 2 and rotate it anti-clockwise to the position shown in FIG. 2B, withdrawing the latch from the door frame. The user will then push or pull the door open, as the case may be, and walk through. Upon release of the handle 2, it will return to its starting position, causing germicidal agent to be applied to the surface of the handle 2, thereby sterilising its surfaces.

The assembly 1 may be adapted for use on a door opening from the right. In that case the handle 2 will protrude toward the right (as opposed to that shown in FIGS. 2A and 2B) and the spray head 4 will be mounted on the right-hand side of the housing 3. In this case, the handle 2 will be rotated clockwise from the horizontal to open the door and will be urged counter-clockwise.

Figure 3A:
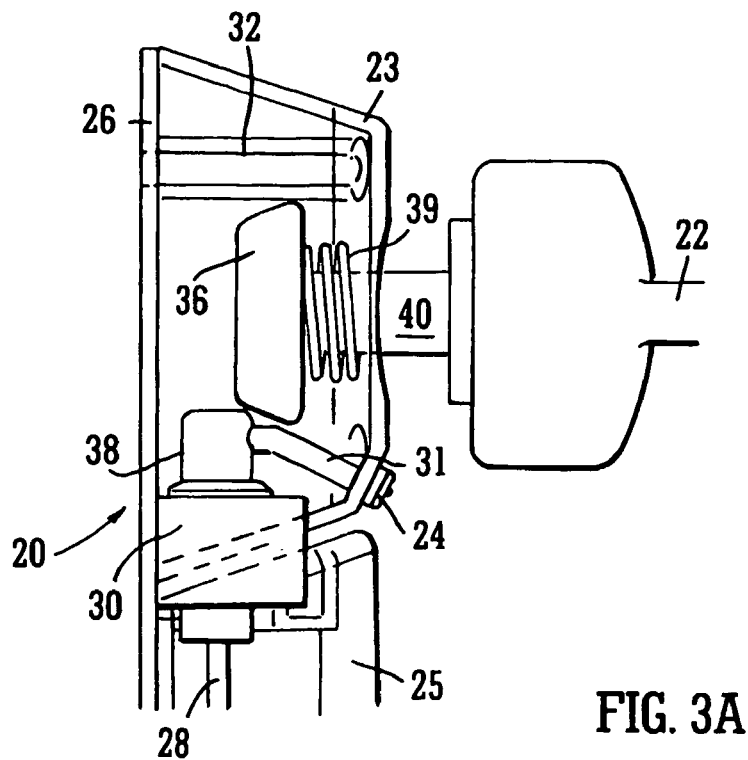
FIGS. 3A and 3B are part sectional views of a second embodiment of handle assembly.
Figure 3B:
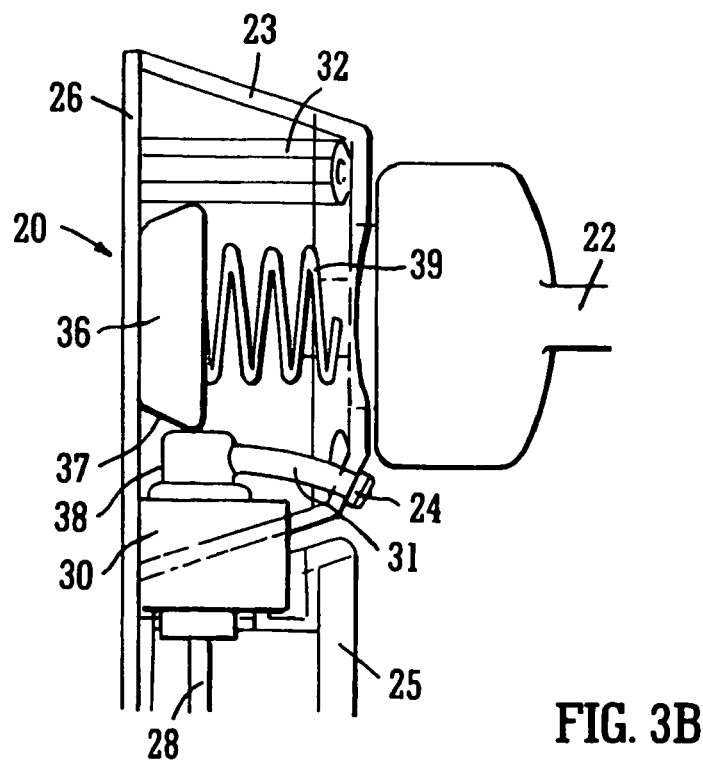

FIGS. 3A and 3B show a second embodiment of handle assembly 20 for a pull handle door. The assembly 20 has a housing 23, a reservoir 25, a handle 22 and a plate 26 to which the housing 23 is mounted, the whole being secured to a door by screws extending through screw holes 32.

Located within the housing 23 is a compression spring 39 and a member 36 which are mounted about a spigot 40 connected to the handle 22. As with the first embodiment of handle assembly 1, a spray head 24 is mounted in the housing 20 and is connected via a flexible tube 31 to a pump head 38, the pump head 38 comprising part of a delivery device 30. Depending from the delivery device 30 is a tube 28 which extends to or near the bottom of the reservoir 25. The pump member has an internal compression spring (not shown), urging it into the position shown in FIG. 3A.

The member 36 has a chamfered perimeter, to give a frusto-conical shape, the perimeter thereof providing an abutment surface 37. The compression spring 39 urges the member 36 to the position shown in FIG. 3B.

To open a door to which the assembly 20 is attached, a user pulls on the handle 22, compressing the spring 39 and allowing the pump head 38 to rise. The rising pump head 38 draws germicidal agent from the reservoir 25, through pipe 28 and into pipe 31. A non-return valve (not shown) within the delivery device 30 prevents fluid in tube 31 from flowing back into tube 28.

As the handle 22 is released, the compression spring 39 urges the member 36 to the left, as shown in FIG. 3B, causing the depression of the pump head 38, thereby forcing germicidal agent out through the spray head 24 and on to the handle 22.

Therefore, as soon as the opener releases the handle 22, after having stepped through the door, germicidal agent is sprayed onto the handle 22 to sterilise it.

Figure 4A:
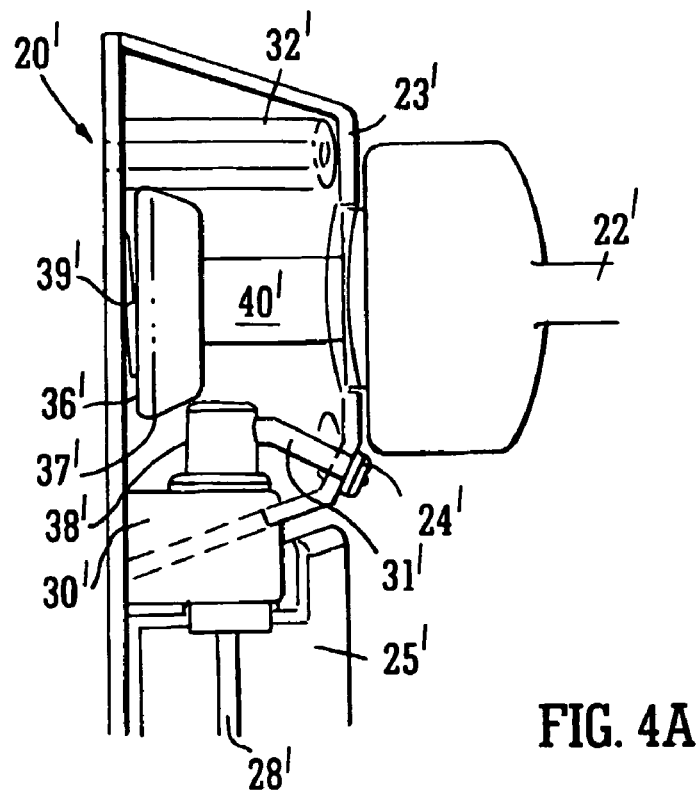
FIGS. 4A and 4B are part-sectional views of a third embodiment of handle assembly.
Figure 4B:
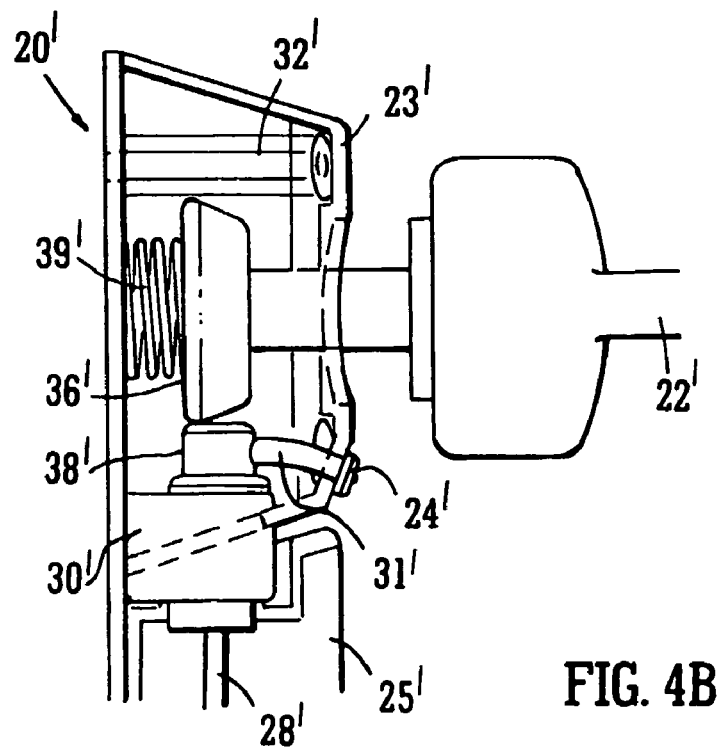

FIGS. 4A and 4B show a door handle similar to that discussed with reference to FIGS. 3A and 3B but for a push door (similar components being denoted by the same number with a prime (')).

To open a door to which the assembly 20' is attached, a user pushes on the handle 22', compressing the spring 39' and allowing the pump head 38' to rise, as shown in FIG. 4A. The rising pump head 38' draws germicidal agent from the reservoir 25', through pipe 28' and into pipe 31'. A non-return valve (not shown) within the delivery device 30' prevents fluid in tube 31' from flowing back into tube 28'.

As the handle 22' is released, the compression spring 39' urges the member 36' to the right, as shown in FIG. 3B, causing the depression of the pump head 38', thereby forcing germicidal agent out through the spray head 24' and on to the handle 22'.

Therefore, as soon as the user releases the handle 22', after having stepped through the door, germicidal agent is sprayed onto the handle 22' to sterilise it.

Whilst the invention with relation to FIGS. 3A, 3B, 4A and 4B has been described as being for either a push or pull door, it will be appreciated that two compression springs 39 and 39' could be mounted within the housing 23 with, say, a diamond-shaped member therebetween, an apex of which being biased into engagement with the pump head 38, 38'. Pushing the handle in either direction will cause the pump head 38, 38' to rise, thereby priming the delivery means. The two compression springs 39 and 39' will urge or bias the member toward a central position. Therefore, release of the handle will cause the diamond-shaped member to adopt the equilibrium position, ensuring the pump member depresses, thereby forcing germicidal agent from the spray head and onto the handle.

Figure 5:
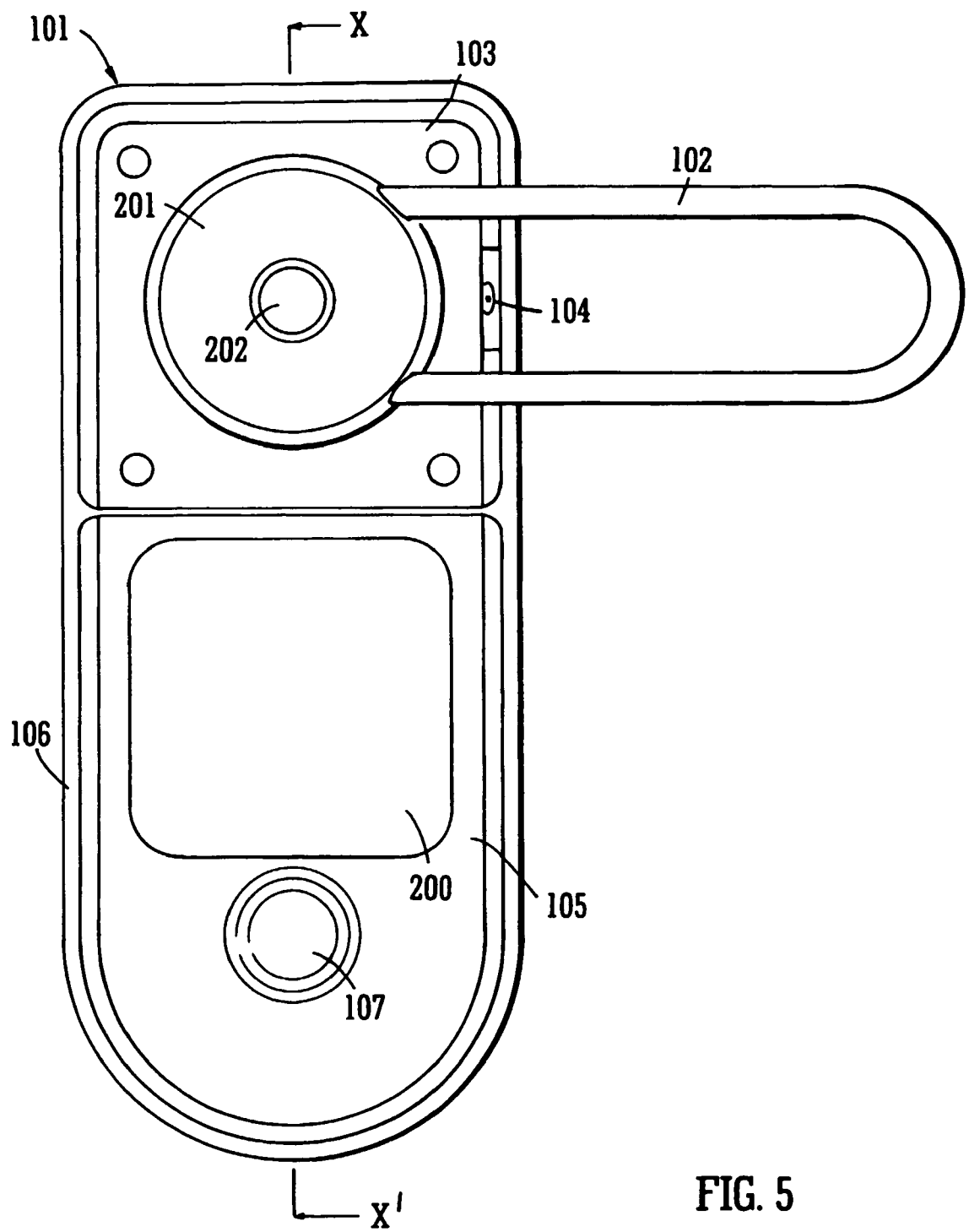
FIG. 5 is an elevation of a modification of the first embodiment.

FIG. 5 shows a handle assembly 101, which is a modification of the handle shown in FIG. 1, having a pivotable handle 102, a housing 103 and a reservoir 105 for holding germicidal agent. The housing 103 and reservoir 105 are mounted or carried on a plate 106. Located on the right-hand side of the housing 103 is a spray head 104. The reservoir 105, which may be either translucent or opaque, is provided with a lock 107. The reservoir 105 may also be provided with a panel 200 for display of indicia, such as advertising and the like.

The handle 102, is attached to a rotatable hub 201. Mounted on the hub 201 is a push button lock 202, as is known in the art, to lock the door when, say a toilet or bathroom is in use.

Figure 6:
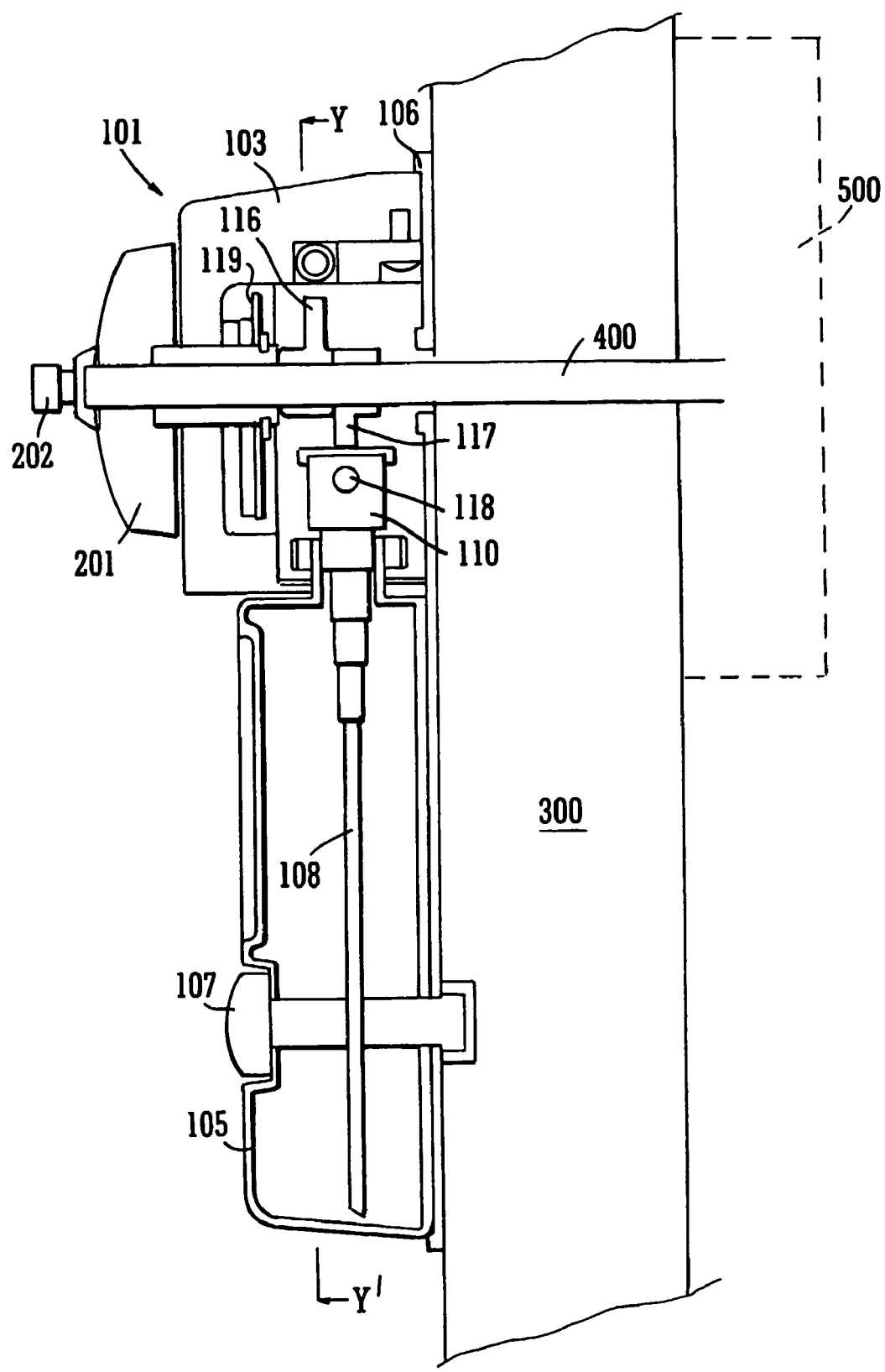
FIG. 6 is a sectional view along line X-X' of FIG. 5.

FIG. 6 shows the assembly 101 mounted on a door 300, with a spindle 400 extending through the door 300 and engaging the assembly 101. A further assembly 101 or conventional door handle 500 may be mounted on the other side of the door.

A torsion spring 119 is mounted about the spindle 400 which resiliently urges the handle 102 to the horizontal position shown in FIG. 5.

A pipe 108 extends from the bottom of the reservoir 105 to a delivery device 110, having a pump head 118. Mounted about the spindle 400 for rotation therewith, are two cam surfaces 116, 117.

Cam surface 117 engages the pump head 118 for dispensing germicidal agent as previously explained. Cam surface 116 is arranged to arrest the return stroke of handle 102 as will be described below.

Figure 7:
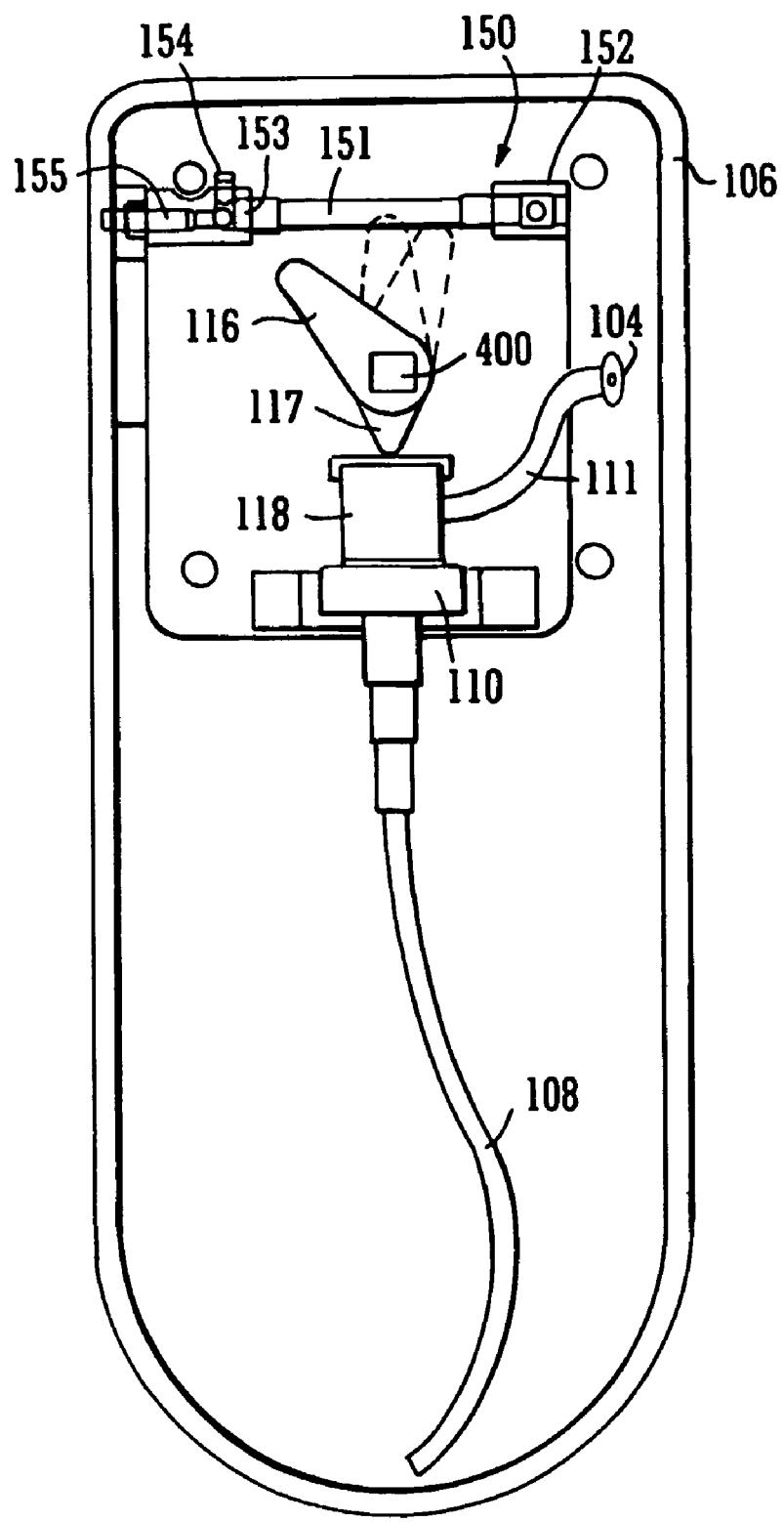
FIG. 7 is a sectional view along line Y-Y' of FIG. 6.
Figure 8:
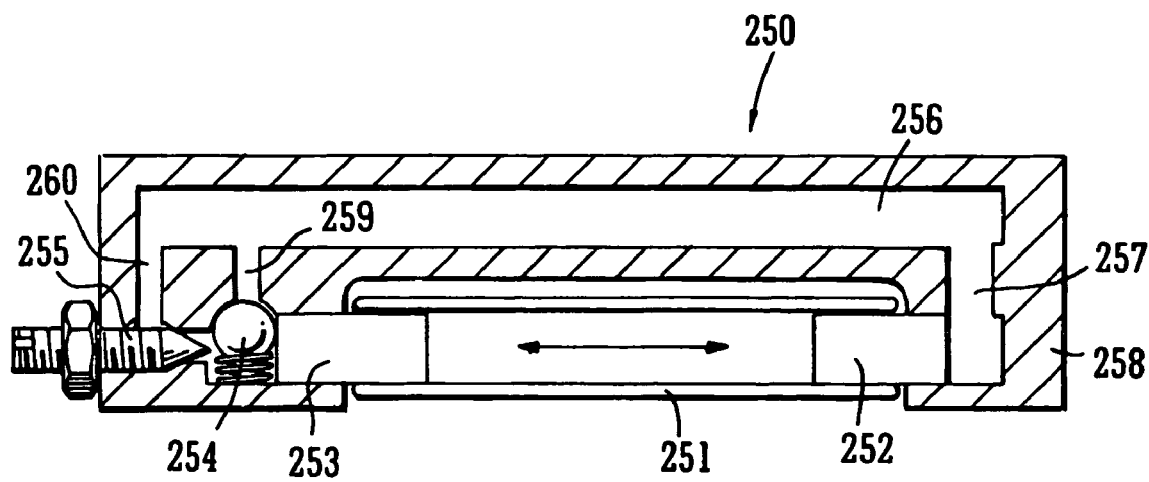
FIG. 8 is a plan view of a retardation device for installation in a modification of the first embodiment.
Figure 9:
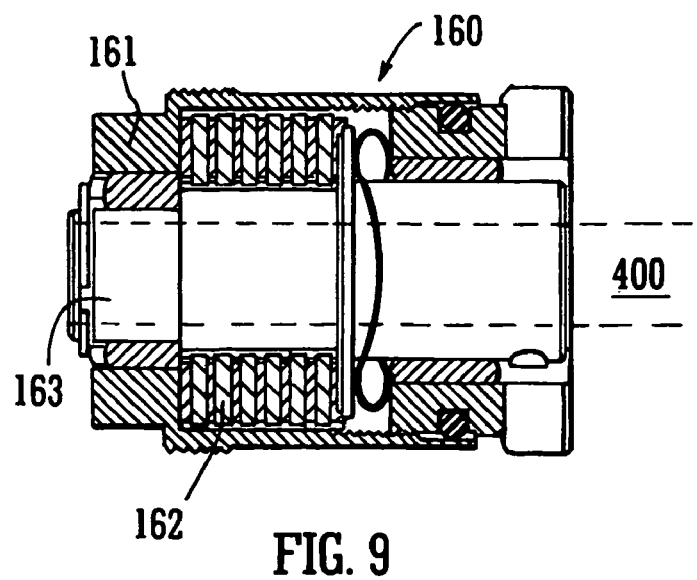
FIG. 9 is a view of a friction clutch for installation in a modification of the first embodiment.

FIG. 7 shows the assembly 101 in the "closed door" position, i.e. with the handle 102 horizontal (as shown in FIG. 5). A relatively short flexible pipe 111 provides fluid connection between the pump head 118 and the spray head 104.

Mounted at the top of the housing 103 is a retardation device 150 comprising a flexible-walled tube 151 held between two hollow mountings 152, 153. Preferably, the flexible-walled tube 151 is formed from PVC or other impact resistant and flexible plastics material. The internal volume of mounting 152 is in communication with the interior of the housing 103, thus flexible-walled tube 151 is in fluid communication with the interior of the housing via mounting 152. Mounting 153 is provided with a resiliently urged ball valve 154 whose principal axis is orthogonal to the axis of the tube 151, and a throttle valve 155, in line with the axis of the tube 151, occluding the path between flexible-walled tube 151 and the interior of the housing 103 via mounting 152.

When an operator opens the door 300 by operating the assembly 101, he grasps the handle 102 and rotates it clockwise. Such rotation causes the hub 201 to rotate and, consequently, the spindle 400, thereby withdrawing the door latch (not shown) from its lock (also not shown) mounted in the door-frame (not shown). Rotation of the handle 102 causes cam surface 117 to rotate clockwise about the spindle 400, thereby disengaging the pump head 118. As the cam surface 117 disengages pump head 118 the head 118 is urged upwards by an internally mounted compression spring (not shown), causing germicidal agent to be drawn from the reservoir 105, through pipe 108 and into pipe 111.

As the spindle 400 rotates, cam surface 116 also rotates and, in so doing, engages and compresses flexible-walled tube 151 forcing the air within the tube 151 to be forced to the right and into the housing 103. The passage of the cam surface 116 in this direction is relatively unrestricted. Simultaneously, air is drawn into the tube 151 through the ball valve 154, which acts as a non-return valve.

When the handle 102 is released, the spring 119 urges the handle 102 towards the horizontal (as shown in FIG. 5). However, as cam surface 116 engages the flexible-walled tube 151, it compresses the walls thereof forcing air towards the left (as shown). The throttle 155 occludes the passageway thereby reducing the flow of air and causing the cam surface 116 and hence cam surface 117 to rotate relatively slowly. As (relatively slow) rotation of the cam surface 116 continues, due to the urging of the spring 119, the cam surface passes by an equilibrium position (shown as being vertical as indicated by the dotted lines) after which the urging of the spring 119 will overcome the resistance offered by the air in the flexible-walled tube 151 and throttle valve 155. Once the resistance offer by the air in the flexible-walled tube 151 has been overcome, the spring 119 causes relatively rapid counter-clockwise rotation of the spindle 400. The relatively rapid rotation of the cam surface 116 brings the cam surface 116 into engagement with the pump head 118, thereby forcing the pump head 118 downwards and thereby ejecting germicidal agent from the spray head 104 and onto the handle 102.

By providing for such retardation of the return stroke of the handle 102, it is less likely that a user will be sprayed with the germicidal agent. Thus a user will operate the handle 102, walk through the door, the handle 102 will start to (slowly) rotate counter-clockwise and will then rotate relatively quickly and deliver a dose of germicidal agent onto the handle 102. The user will have departed.

The degree or extent of retardation of the return stroke is controlled by the throttle 155, which is preferably adjustable. If the throttle 155 is relatively open there will be a lesser degree of retardation and vice versa. The extent of retardation will be determined by the operating conditions of the door and of the site in which it is located.

Clearly, the assembly 101 could be used for left- and right-handed doors by the simple expediency of providing two ports where the spray head 104 can be mounted and by turning the hub 201 so that the handle 102 extends in the opposite direction.

FIG. 8 shows a modified retardation device 250 having a flexible-walled tube 251 held between two hollow mountings 252, 253 to define a passageway, the whole being retained in a casing 258. The casing 258 also defines a bore 256 aligned parallel to the tube 251. The hollow mounting 252 is in unrestricted fluid communication with the bore 256 via passageway 257.

A resiliently urged ball valve 254 and throttle valve 255 are mounted within the casing 258 at an end thereof distant from the passageway 257. The ball of ball valve 254 is urged into engagement with the end of a passage 259 which communicates with the bore 256. The throttle valve 255 at least partially occludes one end of a passage 260, the other end of the passage 260 being in fluid communication with bore 256.

The entire volume defined by the tube 251, mountings 252, 253, bore 256 and passageways 257, 259, 260 is filled with a fluid, say a gas or a liquid such as water, an oil or other hydraulic fluid.

The direction of the movement of the cam 116, in use, with respect to the tube 251 is indicated by the double-headed arrow.

Thus, and taking a right-handed door as shown in FIG. 5 and 7, as the handle is turned clockwise, cam 116 rotates clockwise bringing it into engagement with tube 251. As the walls of the tube 251 are compressed together, continued rotation of the cam 116 causes fluid to be forced towards the right of the tube 251, causing fluid to flow through passage 257, along bore 256 and along passage 259. The pressure of the fluid will act against the spring in ball valve 254 thereby letting fluid flow in to the interior of mounting 253. Because the urging of the ball valve 254 is not very severe, relatively unrestricted flow is afforded the fluid around the closed-loop.

When the handle is released, the internally mounted torsion spring 119 causes the handle to rotate anti-clockwise thereby causing cam 116 to rotate anti-clockwise. As the cam 116 engages the walls of tube 251 it compresses the walls, forcing fluid towards the left. The ball valve 254 acts as a non-return valve. Therefore, the only route for the fluid is via the throttle 255 which occludes the passageway 260, restricting fluid flow around the closed loop and thereby retarding rotation of the cam 116 and, consequently, the handle.

The spring 119 continues to urge the cam 116 counter-clockwise, forcing fluid passed the throttle 255. Once the cam 116 has passed an equilibrium position, say where it is vertical, the walls of the tube 251 will no longer be crushed and fluid is no longer forced in one direction only. At this point, further rotation of the cam 116 will be relatively unrestricted, allowing relatively fast counter clockwise rotation of the cam 116 and cam 117, allowing for depression of pump head 118.

The push and pull handles 22, 22' shown in FIGS. 3A to 4B could be provided with a similar mechanism to that described above, where the retardation device 150, 250 is parallel to the plane of operation of the handle and is mounted for engagement by the upper surface of member 36, 36'.

FIG. 9 shows a further retardation device, in the form of a friction clutch 160 having a housing 161 within which is mounted a rotatable hub 162. The hub 162 has a through-bore 163 which can accept a spindle 400 in a friction fit or may be complementarily shaped to the external shape of the spindle 400. In any case, the hub 162 is arranged to rotate with the spindle 400. The friction clutch 160 allows for controlled slip between the hub 162 and housing 161 when a pre-determined force is exerted but allows free rotation in one direction. Thus, as the handle 102 is turned to open the door 300, the clutch 160 provides no resistance, thereby allowing the cam surface 116 to disengage, and consequently prime, the pump head 118. When the handle is fully turned, the spring 119 will exert maximum force upon the clutch 160. At the maximum force, the clutch 160 slips slowly, allowing for relatively slow rotation between the housing 161 and hub 162. After slipping slowly for a few seconds, the clutch 160 will give, allowing relatively fast rotation of the spindle 400 and causing the cam surface 116 to re-engage the pump head 118, forcing germicidal agent from the spray head 104.

The friction clutch 160 may be mounted at a location distant from the spindle 400 and be operably connected to the spindle 400 by a belt, chain, or the like. A suitable friction clutch 160 may be supplied by Huco Engineering Industries of Hertford, United Kingdom.

Other retardation devices may include a timer switch which forces a pawl to engage cam surface 117 for a pre-set time period, or a resiliently urged ratchet and pawl mechanism to retard the return stroke. In any case, it is necessary that the cam surface 116 engages the pump head 118 with sufficient force to eject a dose of germicidal from the spray head 104, therefore, the return stroke must only be retarded for a small part of its travel.

Whilst a large number of germicidal agents may be used, it is preferred to use one which is rapidly evaporated once it is applied to the surface of the handle 2, 22, 22', 102. In order to use a rapidly evaporating germicidal agent it is necessary that its germicidal action is rapid, necessarily more rapid than the rate of evaporation. Suitable agents are IPA (isopropyl alcohol) and solutions of tea tree oil. A residue of germicidal agent may remain on the handle 2, 22, 22', 102.

In certain circumstances, it may be desired to have a relatively slowly evaporating germicidal agent. Low use doors in areas of potentially high germ concentrations may be such areas.

Applying the germicidal agent as a fine spray or aerosol helps both rapid evaporation, thereby ensuring that users do not get the agent on their hands and also helps the desideratum ensuring that all of the handle's surfaces have the agent applied thereto. Whilst we do not intend to be limited by any particular theory, our investigations that when the mist or aerosol emitted by the spray head 4, 24, 24', 104 is so fine, residual air turbulence caused by the action of the door closing, encourages eddy currents to form. The so-formed whorls and vortices ensure that the germicidal agent is applied to surfaces which are not facing the spray head 4, 24, 24', 104.

On average, a charge 0.05 ml has been found sufficient to spray onto the handle to sterile the surface thereof. Thus a reservoir 5, 25, 25', 105 of 150 ml capacity would spray three thousand times before it is exhausted. The capacity of the reservoir 5, 25, 25', 105 may be matched to the expected 'use-rate' of the door. For example, for a door which is used frequently, a higher volume reservoir 5, 25, 25', 105 may be used to ensure that the reservoir 5, 25, 25', 105 does not run dry and so that it is not necessary to change or fill the reservoir 5, 25, 25', 105 too frequently.

As a cleaner or janitor completes his or her round, it will be a simple task to check the volume of germicidal agent left within the reservoir 5, 25, 25', 105 . If it requires replenishing, the reservoir 5, 25, 25', 105 is simply detached from the housing 3, 23, 23', 103 and re-filled with germicidal agent. Alternatively, the reservoir 5, 25, 25', 105 could be provided as a filled cartridge. In such cases the cleaner or janitor will simply remove an exhausted cartridge from the assembly 1, 20, 20', 101 and replace it with a full one.

The reservoir or cartridge 5, 25, 25' may have indicia such as advertising, instructions for use, instructions for replenishing the reservoir or changing the cartridge printed thereon, for example.

It will be noted that the germicide is applied to the handle as or after it moves to the rest position; that such movement can easily be retarded; the spray of germicide is visible to the user; the sprayed surface will not be wet to touch. The reservoir of germicidal agent may easily be replenished or replaced.

The lock 7, 107 may be provided to prevent unwanted tampering. In certain circumstances the lock 7, 107 will be seen as being unnecessary.

As an alternative to the lock 7, 107, or additionally thereto, a small lamp may be provided within the housing 3, 23, 23', 103 or a phosphorescent panel. The lamp will be actuated upon failure of ambient lighting to ensure that someone within, say, a washroom or toilet, can find the door. A phosphorescent panel will emit a limited amount of light subsequent to failure of ambient lighting. In place of a panel, the reservoir 5, 25, 25', 105 may be formed from a phosphorescent material.

The tab 13 shown in FIGS. 1, 2A and 2B, may be solid or may have apertures formed therein. If solid, it may comprise a scented substance which emits a scent for air-freshening. If it has apertures therein, a scented substance or air-freshener may be located within the housing, the apertures allowing the scent or air-freshener to escape from the housing and in to the surrounding area. The cleaner or janitor will be able to replace the scented substance as part of their normal duties. In some situations, it will be preferred to not have a scented substance therein. In such cases, the tab may act as a plug. Alternatively, the assembly 1 may be absent a tab 13.

It will be realised that the invention is not limited to the embodiments shown. The apparatus may be adapted for mounting on or incorporation in a door handle; the means for spraying the germicide and/or the priming mechanism and the retardation means may each be different from what has been shown. The apparatus operates mechanically but electrical devices may also be used.

Whilst the invention has been described with reference to doors and door handles, it will be appreciated that a resiliently urged tap could likewise be provided with the spray head as described above with reference to FIGS. 1, 2A and 2B and 5 to 7. In public washrooms, taps, especially hot water taps, are often resiliently urged so as to prevent unnecessary wastage of water. Thus, by providing a source of germicidal agent, a spray head, a surface to abut a pump member, the invention could be adapted for use on a tap to disinfect the surfaces thereof after use.

The invention could similarly be applied to a toilet cistern handle. Each of the embodiments discussed could be used in toilet cisterns, with the housing, reservoir and spray head mounted within the cistern and being arranged to spray a germicidal agent onto the handle subsequent to its use.

It will be appreciated that the assembly 1, 20, 20', 101 can be installed on doors for industrial refrigerators, vehicles, such as food delivery vehicles, aircraft and any other doors as well as doors in toilets and washroom facilities.

It will also be appreciated that the handle assemble 1, 20, 20', 101 can be easily and cheaply be retro-fitted to existing doors without the need for extensive modification of the existing door.

Although a specific embodiment of the invention has been disclosed, it will be understood by those having skill in the art that changes can be made to this specific embodiment without departing from the spirit and scope of the invention. The scope of the invention is not to be restricted, therefore, to the specific embodiment, and it is intended that the appended claims cover any and all such applications, modifications, and embodiments within the scope of the present invention.

What is claimed is:

1. A handle for operating one of a door, a faucet and a toilet cistern, comprising a movable member;

a contact surface on the movable member for grasping by a person to move the movable member from a resting position to a second position, the movable member returning to the resting position upon release of the movable member by the person;

germicide applying means for applying the germicide to the contact surface; and an operating mechanism coupled between the movable member and the germicide applying means to cause germicide to be applied to the contact surface, characterised in that the operating mechanism directs a spray of at least one of an aerosol and a mist of germicide onto the contact surface during a return movement of the movable member to the resting position such that the spray is produced only after the movable member is released by the person, thereby allowing the spray to land on substantially all of the contact surface and not on the person.

2. The handle as claimed in claim 1, further comprising retarding means are provided for retarding the return movement of the movable member to the resting position after manual release of the contact surface.

3. The handle according to claim 2, wherein the germicide applying means comprises a reservoir for containing the germicide and a pump connected between the reservoir and an outlet for spraying onto the contact surface germicide received from the reservoir via the pump.

4. The handle according to claim 3, wherein the operating mechanism is operable to prime the pump with the germicide during the movement of the movable member from the resting position to the second position.

5. The handle according to claim 4, wherein the pump further comprises an operating element movable to prime the pump and further movable to eject germicide, the operating mechanism being operable in response to the movement and the return of the movable member to move the operating element of the pump.

6. The handle according to claim 5, wherein the operating mechanism further comprises a camming member mounted for turning movement in response to the movement and the return of the movable member, the camming member having a camming surface engaged with the operating element.

7. The handle according to claim 3, wherein the movable member comprises a resiliently urged surface; and wherein the germicide applying means comprises germicide delivery means and a source of germicide and the resiliently urged surface is movable between the first position where it engages the delivery means and the second position where it is not in engagement with the delivery means, wherein the handle is operable to urge the resiliently urged surface from the first position to the second position thereby priming the delivery means with a charge of germicide from the source of germicide, the return of the handle to the resting position causing the resiliently urged surface to adopt the first position, whereby germicide is applied to the handle.

8. A self-sterilizing handle assembly for a door comprising:

a manually operable handle and a spray head, the handle being operable to open the door, characterised in that the handle is arranged, upon manual release of the handle by a user subsequent to operation of the door, to cause the spray head to spray germicide over at least part of the handle, characterized in that movement of the handle subsequent to the manual release of the handle is controlled by a retardation device, the retardation device comprising a flexible-walled tube and a cam that engages the flexible-walled tube and compresses the wall of the flexible-walled tube thereby causing air within the flexible-walled tube to move.

9. A door handle assembly, comprising:

a handle capable of being secured to a door and having a contact surface for enabling the handle to be moved manually by a user, against action of a spring, from a resting position to a second position in order to operate a door catch to permit the door to be opened, wherein the handle returns to the resting position from the second position after the contact surface of the handle has been released by the user; and means for automatically disinfecting the contact surface of the handle each occasion the door catch is operated, wherein the means for automatically disinfecting includes a germicide reservoir and a pumping mechanism operated by movement of the handle and operative to spray germicide drawn from the germicide reservoir directly onto the contact surface of the handle only during a return movement of the handle from the second position to the resting position.

* * * * *